(12) United States Patent
Kennedy et al.

(10) Patent No.: US 11,883,459 B2
(45) Date of Patent: Jan. 30, 2024

(54) THIOL ISOMERASES INHIBITORS FOR THE TREATMENT AND PREVENTION OF FOOD ALLERGIES, ALLERGIC DISEASES, AND INFLAMMATORY DISEASES

(71) Applicant: WESTERN NEW ENGLAND UNIVERSITY, Springfield, MA (US)

(72) Inventors: Daniel Kennedy, Longmeadow, MA (US); Clinton Mathias, Wilbraham, MA (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 0 days.

(21) Appl. No.: 16/971,186

(22) PCT Filed: Feb. 20, 2019

(86) PCT No.: PCT/US2019/018679
§ 371 (c)(1),
(2) Date: Aug. 19, 2020

(87) PCT Pub. No.: WO2019/164874
PCT Pub. Date: Aug. 29, 2019

(65) Prior Publication Data
US 2021/0128679 A1 May 6, 2021

Related U.S. Application Data (60) Provisional application No. 62/632,717, filed on Feb. 20, 2018.

(51) Int. Cl.
| | | |
|---|---|---|
| A61K 38/00 | (2006.01) | |
| A61K 38/12 | (2006.01) | |
| A61P 37/08 | (2006.01) | |
| A61K 31/381 | (2006.01) | |
| A61K 31/7048 | (2006.01) | |
| A61K 45/06 | (2006.01) | |

(52) U.S. Cl.
CPC ............ *A61K 38/12* (2013.01); *A61K 31/381* (2013.01); *A61K 31/7048* (2013.01); *A61K 45/06* (2013.01); *A61P 37/08* (2018.01)

(58) Field of Classification Search
CPC .. A61K 31/381; A61K 31/7048; A61K 38/12; A61K 45/06; A61K 39/35; A61K 9/50; A61P 37/08; G01N 33/68
See application file for complete search history.

(56) References Cited

U.S. PATENT DOCUMENTS

| | | |
|---|---|---|
| 5,792,506 A | 8/1998 | Buchanan et al. |
| 6,190,723 B1 | 2/2001 | Buchanan et al. |
| 2005/0032173 A1 | 2/2005 | Rojas et al. |
| 2007/0190069 A1 | 8/2007 | Koppelman |
| 2012/0157417 A1 * | 6/2012 | Baroni ............... A61P 29/00 514/166 |
| 2016/0145209 A1 | 5/2016 | Flaumenhaft et al. |
| 2019/0076521 A1 | 3/2019 | Matsunaga et al. |

FOREIGN PATENT DOCUMENTS

| | | | |
|---|---|---|---|
| WO | 9612799 A1 | 5/1996 | |
| WO | 0058352 A2 | 10/2000 | |
| WO | 0058453 A2 | 10/2000 | |
| WO | 0070064 A1 | 11/2000 | |
| WO | 2005060994 A1 | 7/2005 | |
| WO | WO-2008100539 A1 * | 8/2008 | ............... A61P 1/00 |
| WO | WO-2013116798 A2 * | 8/2013 | ......... A61K 2300/00 |
| WO | 2018140858 A1 | 8/2018 | |
| WO | WO-2018140858 A1 * | 8/2018 | ........... A61K 31/198 |

OTHER PUBLICATIONS

Jasuja et al. Protein disulfide isomerase inhibitors constitute a new class of antithrombotic agents. J Clin Invest. Jun. 1, 2012; 122(6): 2104-2113 (Year: 2012).*
Mlcek et al. Quercetin and Its Anti-Allergic Immune Response. Molecules. May 2016; 21(5): 623. (Year: 2016).*
Choi et al. A novel multifunctional peptide oligomer of bacitracin with possible bioindustrial and therapeutic applications from a Korean foodsource Bacillus strain. PLoS One. 2017; 12(5): e0176971 (Year: 2017).*
Merck manual. Peter Delves. Overview of Allergic and Atopic Disorders. Accessed Jul. 9, 2021. (Year: 2020).*
Pahwa et al. Chronic Inflammation. StatPearls—NCBI Bookshelf (Year: 2020).*
Healthline. Understanding and Managing Chronic Inflammation. Seunggu Han, M.D. Accessed Dec. 29, 2020. (Year: 2018).*
Chen et al. Inflammatory responses and inflammation-associated diseases in organs. Oncotarget, 2018, vol. 9, (No. 6), pp. 7204-7218. (Year: 2018).*
Dinarello. Grand challenge in inflammation. Front. Immunol., Feb. 14, 2012 (Year: 2012).*
Alloza et al. The metallopeptide antibiotic bacitracin inhibits interleukin-12 ab and b2 secretion. JPP 2005, 57: 213-218 (Year: 2005).*
Choi et al. 2013. Rutin suppresses atopic dermatitis and allergic contact dermatitis. Experimental Biology and Medicine 2013; 238: 410-417 (Year: 2013).*
Takahashi et al. (Allergy, Asthma & Clinical Immunology 2014, 10:3). New efficacy of LTRAs (montelukast sodium): it possibly prevents food-induced abdominal symptoms during oral immunotherapy (Year: 2014).*
Xiao et al. (Inflammation, vol. 41, No. 2, Apr. 2018. Protein Disulfide Isomerase Silence Inhibits Inflammatory Functions of Macrophages by Suppressing Reactive Oxygen Species and NF-kB Pathway (Year: 2018).*
Andersson et al. Clin Exp Immunol 1996; 104 (Suppl. I): 10-20. Intravenous immune globulin affects cytokine production in T lymphocytes and monocytes/macrophages (Year: 1996).*

(Continued)

*Primary Examiner* — Aradhana Sasan
*Assistant Examiner* — Mercy H Sabila
(74) *Attorney, Agent, or Firm* — CANTOR COLBURN LLP (57) ABSTRACT

Disclosed are methods of treating, inhibiting, or preventing the development of, a food allergy in a patient by administering a therapeutically effective amount of a thiol isomerase inhibitor to a patient in need thereof. Also disclosed are methods for treatment of other allergic diseases and inflammatory diseases.

9 Claims, 4 Drawing Sheets

(56) References Cited

OTHER PUBLICATIONS

Aalberse, Rob. C. et al.; "IgG4 breaking the rules"; Immunology, 2002, V. 105, p. 9-19.
Buchanan, B. B. et al.; "Thioredoxin-linked mitigation of allergic responses to wheat" Proc. Natl. Acad. Sci., vol. 94, May 1997, pp. 5372-5377.
Buchanan, Bob B.; "Thioredoxin and food allergy"; J. Allergy Clin Immunol, V. 119*2); p. 513-514, 2007.
Dickerhof, Nina et al.; "Bacitracin inhibits the reductive activity of protein disulfide isomerase by disulfide bond formation with free cysteines in the substrate-binding domain"; The FEBS Journal, 278, 2011; 2034-2043.
Golias, Jaroslav et al.; "Identification of Rice Proteins Recognized by the IgE Antibodies of Patients with Food Allergies"; Journal of Agricultural and Food Chemistry, 2013, V. 61, p. 8851-8860.
Henry, Abigail et al.; "Identifying Novel Small Molecule Inhibitors of ERp57 through a Medium Sized High Throughput Screen" American Association of Colleges of Pharmacy Annual Meeting—Boston, Massachusetts—Jul. 2018 2018 AACP ERP57 inhibitor.
Hoffman, Sidra M. et al.; "Protein disulfide isomerase-endoplasmic reticulum resident protein 57 regulates allergen-induced airways inflammation, fibrosis, and hyperresponsiveness". J Allergy Clin Immunol, vol. 137, No. 3, p. 822-832.e7.
Holbrook, L et al.; "The identification & characterization of a novel, selective ERp57 inhibitor that modulates platelet function through integrin allbβ3 outside-in signalling dep & indep mech"; ICMR V 1: p. 1255. (Abstract Jul. 2017 first published Jun. 23, 2017) doi:10.1002/rth2.12012 2017 ISTH CGP.
Holbrook, L. et al.; "The anti-asthma therapeutic zafirlukast is a broad spectrum thiol isomerase inhibitor that inhibits platelet function"; ICMR, Research and Practice in Thrombosis and Haemostasis. (Abstract Jul. 2017 first published Jun. 23, 2017) vol. 1: p. 1272. doi:10.1002/rth2.12012 2017 ISTH ZFL.
International Search Report for International Application No. PCT/US2019/18679, International Filing Date Feb. 20, 2019, dated May 8, 2019, 5 pages.
Long M. Alissa et al; "Exploring the Role of the Thiol Isomerase ERp57 in Cancer Progression Using Novel Small Molecule Inhibitors"; Jul. 2016 2016 AACP ERp57 Jul. 2016.
Merritt, Jennifer A. et al.; "Exploring Thiol Isomerase Enzymes in Cancer Progression" American Journal of Pharmaceutical Education: vol. 84, Issue 6, Article 8221. (Jul. 2020) 2020 AACP Cancer Cell Effects.
Pantos, Megan M. et al.; "Exploring Montelukast as a Potential Broad Spectrum Thiol Isomerase Inhibitor"; American Journal of Pharmaceutical Education: vol. 83, Issue 5, Article 7654. (Jul. 2019) 2019 AACP Montelukast.
Pantos, Megan M. et al.; "Exploring Zafirlukast for the Inhibition of Platelets, Cancer Cell Growth and Factor Xa Generation"; American Journal of Pharmaceutical Education: vol. 84, Issue 6, Article 8221, Jul. 2020, 2020 AACP Cancer Induced Thrombosis.
Polukort, Stephanie H. et al; "Inhibition of protein disulfide isomerases suppresses mast cell activation and function during food allergy"; American Journal of Pharm Education vol. 82, Issue 5, Article 7158. (Jul. 21-25, 2018) 2018 AACP Food Allergy.
Satoh-Cruz, Sio et al.; "Protein Disulfi de Isomerase Like 1-1 Participates in the Maturation of Proglutelin Within the Endoplasmic Reticulum in Rice Endosperm"; Plan Cell Physiol., 51(9): 1581-1593, 2010.
Stegmann, Monika et al.; "Immunoregulation through membrane proteins modified by reducing conditions induced by immune reactions"; Eur. J. Immunol., V 43, 2013, p. 15-21.
Takaiwa, Fumio et al; "Deposition of a recombinant peptide in ER-derived protein bodies by retention with cysteine-rich prolamins in transgenic rice seed"; PLanta, 2009 V. 229, p. 1147-1158.
Tuckova, Ludmila et al.; "Rice proteins recognized by immunoglobulin E antibodies of patients with food allergies"; Clinical and Translational Allergy, 2014 4(Suppl 2).
Verbetsky, Christina A. et al.; "Zafirlukast Inhibits Cancer Cell Growth via Inhibition of Thiol Isomerase Activity"; American Journal of Pharmaceutical Education vol. 82, Issue 5, Article 7158. (Jul. 2018) 2018 AACP Zafi cancer.
Verbetsky, Christina, A. et al.; "Exploring The Effect of a PDI Inhibitor on Cellular Model of Cancer Induced Thrombosis After Chemotherapy"; American Journal of Pharmaceutical Education: vol. 83, Issue 5, Article 7654. (Jul. 2019) 2019 AACP Factor Xa.
Written Opinion for International Application No. PCT/US2019/18679, International Filing Date Feb. 20, 2019, dated May 8, 2019, 6 pages.

* cited by examiner

THIOL ISOMERASES INHIBITORS FOR THE TREATMENT AND PREVENTION OF FOOD ALLERGIES, ALLERGIC DISEASES, AND INFLAMMATORY DISEASES

CROSS-REFERENCE TO RELATED APPLICATIONS

This Application is a U.S. National Stage Application of International Application No. PCT/US2019/018679, filed Feb. 20, 2019, which claims the benefit of U.S. Provisional Application No. 62/632,717, filed Feb. 20, 2018, each of which is incorporated by reference in its entirety for all purposes.

STATEMENT REGARDING FEDERALLY SPONSORED RESEARCH OR DEVELOPMENT

This invention was made with government support under Grant AI107668 awarded by the National Institute of Allergy and Infectious Diseases (NIAID), National Institutes of Health. The government has certain rights in the invention.

BACKGROUND

Mast cells mediate inflammatory responses such as hypersensitivity and allergic reactions through the release of proinflammatory cytokines. Since mast cells play a role in allergy, it makes them attractive candidates for targeting allergic diseases. Well-known food allergens are found in milk, peanuts, egg, and shellfish. Symptoms of a food allergy reaction can include digestive problems (vomiting, stomach cramps), hives, or swollen airways. Severe reactions can be life-threatening (anaphylaxis).

Thiol isomerases are members of a large family of disulfide oxidoreductases, which catalyze the posttranslational disulfide exchange necessary for the proper folding of newly synthesized proteins. Approximately twenty members of a large family of thiol isomerase/disulfide oxidoreductases exist in humans with a domain composition of thiol isomerases is a-b-b'-a'. These thiol isomerases are generally capable of oxidation reduction and isomerization reactions and are often found in the endoplasmic reticulum where they catalyze the proper folding of newly translated proteins.

Thiol isomerases include protein disulfide isomerase (PDI), ERp5, ERp57, ERp72 and thioredoxin (TRX). These five thiol isomerases have recently been discovered to perform extracellular functions and are henceforth referred to as extracellular thiol isomerases.

Thiol isomerases are endoplasmic reticulum proteins that regulate oxidative protein folding by catalyzing the breakage and reformation of disulfide bonds. Besides catalyzing thiol-disulfide exchange and mediating folding of newly synthesized proteins, thiol isomerases function as molecular chaperones.

There remains a need in the art for new strategies to inhibit or prevent the formation of food allergies. In addition, there is a need to develop therapeutic agents that either prevent sensitization to food antigens or suppress the allergic response after initiation.

SUMMARY

In an embodiment, a method of treating, inhibiting, or preventing the development of, a food allergy in a patient, comprises administering a therapeutically effective amount of a thiol isomerase inhibitor to a patient in need thereof.

In another embodiment, a method of inhibiting or preventing cytokine production in a patient, the cytokine production caused by a food allergen, the method comprises administering a therapeutically effective amount of a thiol isomerase inhibitor to a patient in need thereof.

DRAWINGS

Referring now to the figures, which are exemplary embodiments and not to be considered limiting.

FIG. 1A IL-4, FIG. 1B IL-13, FIG. 1C TNF-alpha, and FIG. 1D IL-6.

FIG. 2A IL-13, FIG. 2B TNF-alpha, and FIG. 2C IL-6.

FIGS. 3A-3F illustrate data for the inhibition of mast cell-mediated food allergy in mice using PDI inhibitor PACMA-31; FIG. 3A serum mMCP-1 levels, FIG. 3B serum OVA-IgE levels, FIG. 3C IL-5 levels, FIG. 3D IL-13 levels, FIG. 3E IL-4 levels, and FIG. 3F IFN-g levels.

DETAILED DESCRIPTION

Disclosed herein are methods of using thiol isomerase inhibitors, particularly protein disulfide isomerase (PDI) inhibitors to treat, inhibit, or prevent the development of, food allergies. It has been found that thiol isomerase inhibitors and particularly PDI inhibitors can suppress or stop the activation of mast cells and prevent or inhibit the formation of mast cell activated cytokines during food allergy.

In an embodiment, a method of treating, or preventing the development of, a food allergy in a patient comprises administering a therapeutically effective amount of a thiol isomerase inhibitor, specifically a protein disulfide isomerase (PDI) inhibitor, to a patient in need thereof.

In an embodiment, a method of inhibiting or preventing cytokine production in a patient, wherein the cytokine production is caused by a food allergen, the method comprises administering a therapeutically effective amount of a thiol isomerase inhibitor, specifically a protein disulfide isomerase (PDI) inhibitor, to a patient in need thereof.

In an embodiment, the patient can be sensitized to a food allergen. In another embodiment, the patient can be at risk of developing a food allergy.

As sentinel cells that sense danger in the form of pathogens or other types of injury at the onset of inflammation, mast cells play a pivotal role in initiating and propagating immune responses. Dysregulated mast cell function is a prominent feature of allergic responses. Mast cells are not only implicated in food allergy, but also other allergic diseases such as asthma, allergic rhinitis, systemic anaphylaxis, atopic dermatitis, and the like. In addition, mast cells have been critically implicated in the pathology of many other inflammatory diseases including rheumatoid arthritis, ulcerative colitis, and cancer.

In an embodiment, a method of treating asthma, allergic rhinitis, systemic anaphylaxis, atopic dermatitis, an inflammatory disease such as rheumatoid arthritis, ulcerative colitis, and cancer in a patient comprises administering a therapeutically effective amount of a thiol isomerase inhibitor, specifically a protein disulfide isomerase (PDI) inhibitor, to a patient in need thereof.

In an embodiment, a method of inhibiting or preventing cytokine production in a patient, the method comprises administering a therapeutically effective amount of a thiol isomerase inhibitor, specifically a protein disulfide isomerase (PDI) inhibitor, to a patient in need thereof.

Within these methods, the patient is an animal, specifically a mammal, including a human, livestock, a companion animal, and the like. In an embodiment, the patient is a human.

Exemplary thiol isomerase inhibitors, including PDI inhibitors, for use in the methods disclosed here include a compound in the class of propynoic acid carbamoyl methyl amides (PACMAs), e.g., PACMA 31 (N-(2,4-dimethoxyphenyl)-N-(1-oxo-2-propyn-1-yl)-2-(2-thienyl)glycylglycine ethyl ester); bacitracin; juniferdin; juniferdin epoxide; rutin (rutoside, quercetin-3-O-rutinoside); phenylarsine oxide; CCF 642 (3-(4-methoxyphenyl)-5-[(5-nitro-2-thienyl)methylene]-2-thioxo-4-thiazolidinone); P1 (N-[(1,1-dimethylethoxy)carbonyl]-L-phenylalanyl-O-(ethenylsulfonyl)-N-4-pentyn-1-yl-L-tyrosinamide); 16F16 (2-(2-chloroacetyl)-2,3,4,9-tetrahydro-1-methyl-1H-pyrido[3,4-b]indole-1-carboxylic acid methyl ester); ML359 (ethyl 1-(3-chloro-4-hydroxybenzyl)-4-(2-phenoxyethyl)piperidine-4-carboxylate); curcumin; zafirlukast; montelukast; CGP-13501 (CAS Reg. No. 56189-68-5); CGP-7930 (CAS Reg. No. 57717-80-3); alosetron; balsalazide; benserazide; butaclamol; leva-dopa; mesalazine; oxcarbazepine; combination thereof and the like; PDI targeting antibodies such as PDI Antibody (RL90, MA3-019); intravenous immunoglobulin (IVIG); combinations thereof and the like.

In an embodiment, the PDI inhibitor is bacitracin, rutin, PACMA 31, a pharmaceutically acceptable salt thereof, or a combination thereof, optionally in combination with curcumin. PACMA 31, N-(2,4-dimethoxyphenyl)-N-(1-oxo-2-propyn-1-yl)-2-(2-thienyl)glycylglycine ethyl ester, is a known orally bioavailable, selective inhibitor ($IC_{50}$=10 µM) of protein disulfide isomerase (PDI).

PACMA 31

The term "active agent", as used herein, means a compound (including the thiol isomerase inhibitor), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline (i.e. amorphous) forms, and any polymorphs of the compound are included. All forms are contemplated herein regardless of the methods used to obtain them.

The term "pharmaceutically acceptable salt", as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The thiol isomerase inhibitor can be administered as the neat chemical, or administered as a pharmaceutical composition. Accordingly, an embodiment provides pharmaceutical compositions comprising a thiol isomerase inhibitor or a pharmaceutically acceptable salt thereof, together with a pharmaceutically acceptable carrier. The pharmaceutical composition may contain a thiol isomerase inhibitor or pharmaceutically acceptable salt thereof as the only active agent, or may contain one or more additional active agents.

The thiol isomerase inhibitor may be administered orally, topically, parenterally, by inhalation or spray, sublingually, transdermally, via buccal administration, rectally, as an ophthalmic solution, or by other means, in dosage form containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, an injectable, or an ophthalmic solution. Some dosage forms, such as tablets and capsules, can be subdivided into suitably sized unit doses containing appropriate quantities of the active components, e.g., an effective amount to achieve the desired purpose.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. An exemplary dosage form is a solid oral dosage form.

The term "pharmaceutical compositions", as used herein, are compositions comprising at least one active agent or a pharmaceutically acceptable salt thereof, and at least one other substance, such as a carrier. Pharmaceutical compositions meet the U.S. FDA's GMP (good manufacturing practice) standards for human or non-human drugs. The pharmaceutical compositions can be formulated into a dosage form.

The term "carrier", as used herein, applied to pharmaceutical compositions refers to a diluent, excipient, or vehicle with which an active compound is provided.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the thiol isomerase inhibitor.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional additional active agents may be included in a pharmaceutical composition, which do not substantially interfere with the activity of the thiol isomerase inhibitor.

The pharmaceutical compositions can be formulated for oral administration. These compositions contain between 0.1 and 99 weight percent ("wt. %") of the thiol isomerase inhibitor, specifically at least about 5 wt. %. In some embodiments, the composition contains from about 25 wt. % to about 50 wt. % or from about 5 wt. % to about 75 wt. % of the thiol isomerase inhibitor.

The term "therapeutically effective amount" of thiol isomerase inhibitor, as used herein, means an amount effective, when administered to a patient, to provide a therapeutic benefit such as a prevention, inhibition, or an amelioration of symptoms, e.g., to prevent the activation of mast cells and prevent the formation of mast cell activated cytokines in a patient suffering from, or susceptible to, a food allergy. A therapeutically effective amount may vary according to factors such as the health, age, and weight of the patient, and the ability of the compound to elicit a desired response in the patient. Dosage regimens may be adjusted to provide the optimum therapeutic response. A therapeutically effective amount is also one in which any toxic or detrimental effects (e.g., side effects) of the thiol isomerase inhibitor are outweighed by the therapeutically beneficial effects.

In an embodiment, the thiol isomerase inhibitor is administered to the patient for a time period sufficient to provide a prophylactically or therapeutically effective result. In an embodiment, the thiol isomerase inhibitor can be administered prophylactically or therapeutically. In another embodiment, the thiol isomerase inhibitor can be administered after an allergic reaction has occurred in the patient as a means of suppressing the activation of mast cells and the formation of mast cell activated cytokines during food allergy thereby suppressing allergy symptoms. The administration can be conducted daily for several days (for example about 2 to about 7 days), for several weeks (for example about 1 to about 4 weeks, specifically about 2 or about 3 weeks), or for several months (for example about 1 to about 36 months, specifically about 2 to about 24 months, and yet more specifically about 6 to about 12 months).

In an embodiment, the thiol isomerase inhibitor is administered to the patient prior to consumption of a food allergen.

In an embodiment, the thiol isomerase inhibitor is administered to the patient after the consumption of a food allergen.

This invention is further illustrated by the following examples that should not be construed as limiting.

EXAMPLES

Example 1.: PDI Inhibitors Bacitracin and Rutin Inhibit Cytokine Production from Activated Mast Cells In this study, bone marrow-derived mast cells (BMMCs) were treated with the known PDI inhibitors bacitracin and rutin, and mast cell activation was assessed. BMMCs were generated from BALB/c mice and grown in 10 ng/ml IL-3 and 10 ng/ml stem cell factor (SCF) for 4-8 weeks. One million BMMCs in triplicates were cultured with various concentrations of the PDI inhibitors Bacitracin (Bac) and Rutin (RH) for 1 day or 7 days. Some cells were activated by priming cells with DNP-IgE (Dinitrophenyl IgE) antibodies and challenging with DNP-BSA (dinitrophenyl-bovine serum albumin). Cytokine levels (IL-4, IL-13, TNF-alpha, and IL-6 in FIGS. 1A-1D, respectively) were assessed in the supernatants 24 hr later by ELISA. FIG. 1A-1D show treatment of mast cells with PDI inhibitor Bacitracin or Rutin inhibits the activation of mast cells and the production of mast cell cytokines such as TNF-a, IL-6, and IL-13.

Figure 1A:
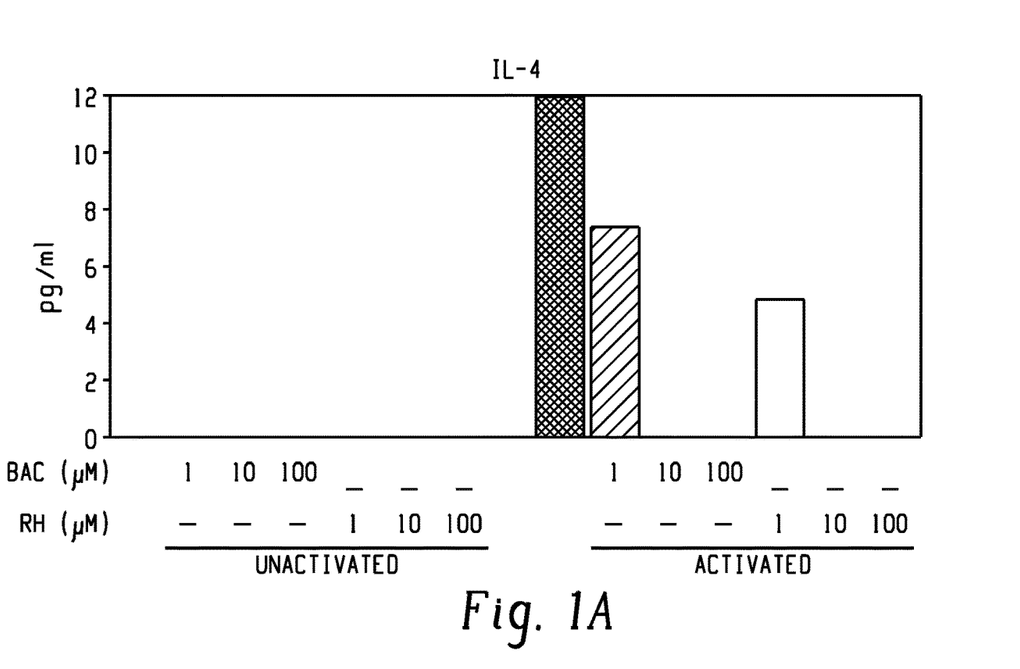
FIGS. 1A-1D illustrate data for the inhibition of cytokine production from activated mast cells using PDI inhibitors bacitracin and rutin.
Figure 1B:
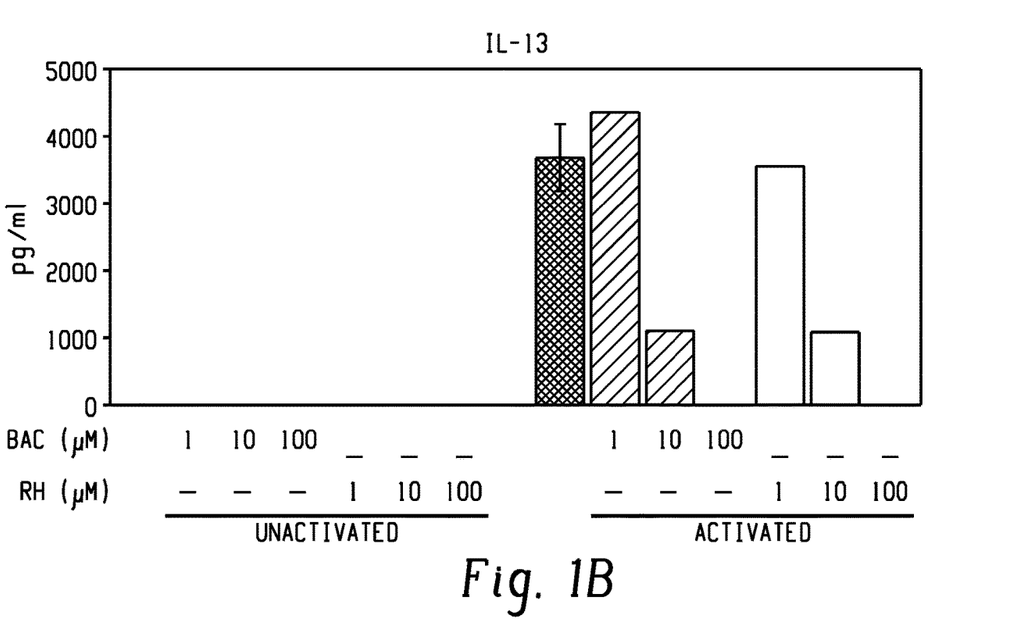
Figure 1C:
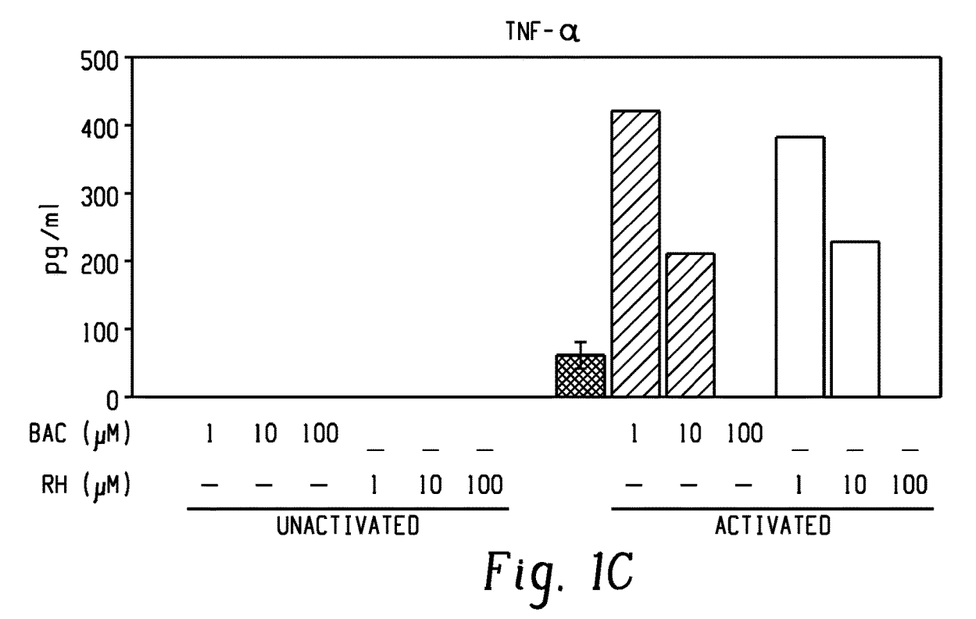
Figure 1D:
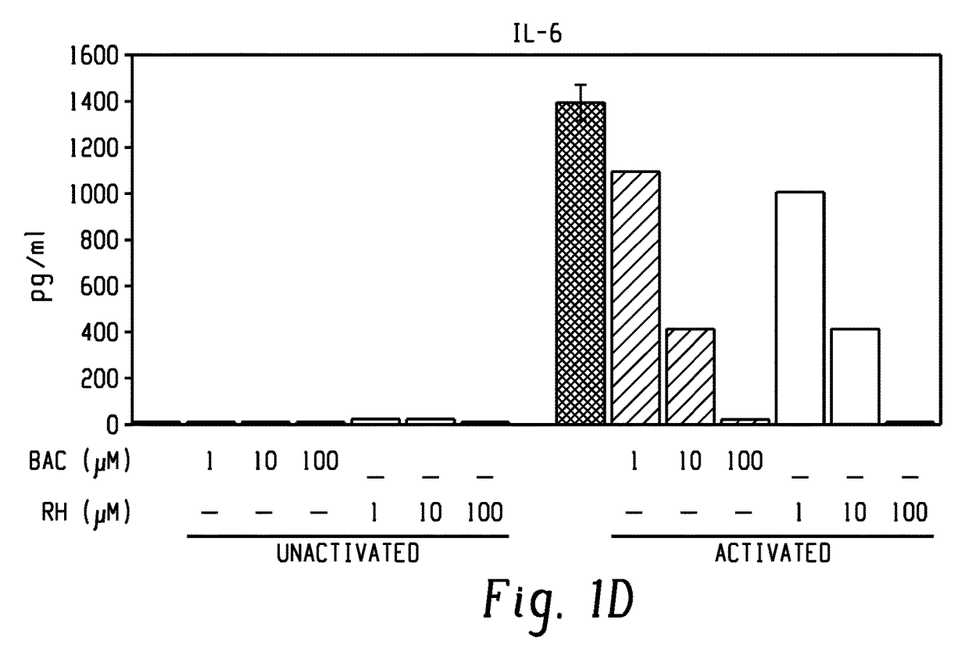
Figure 2A:
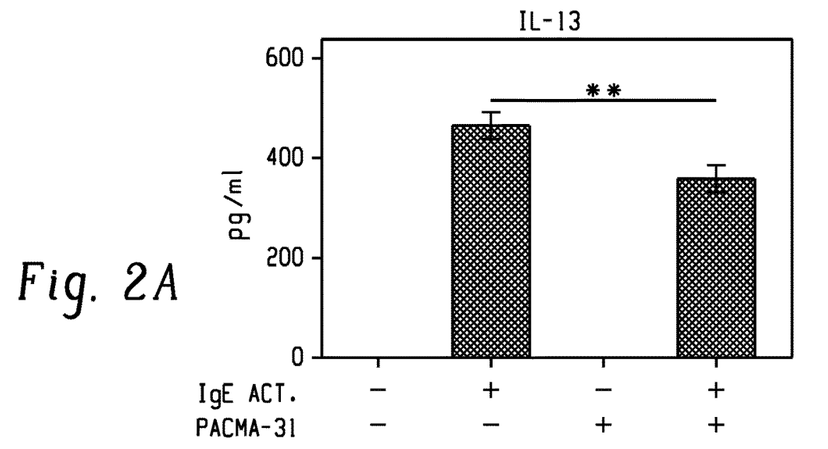
FIGS. 2A-2C illustrate data for the inhibition of cytokine production from activated mast cells using PDI inhibitor PACMA-31.
Figure 2B:
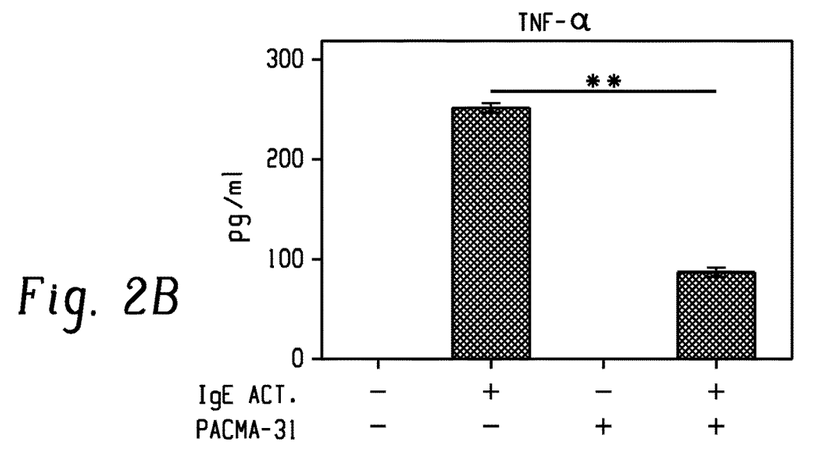
Figure 2C:
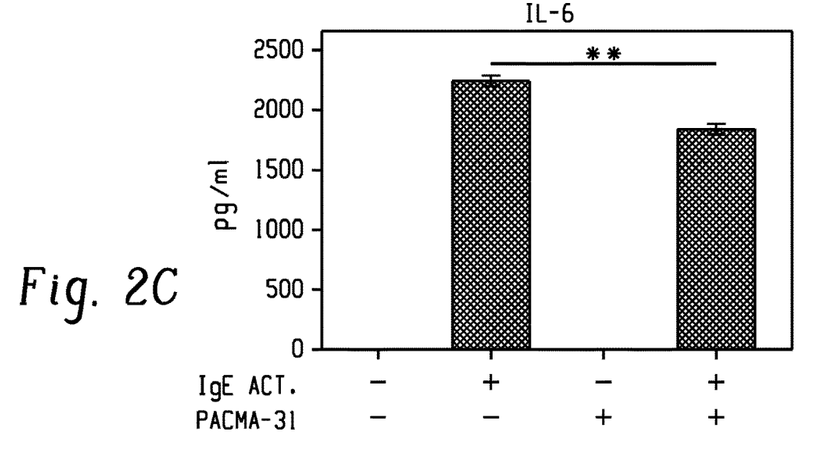

Example 2.: Specific PDI Inhibitor PACMA-31 Inhibits Cytokine Production from Activated Mast Cells In this study, BMMCs were treated with the known PDI inhibitor PACMA-31, and mast cell activation was assessed. Bone marrow derived mast cells (BMMCs) were generated from BALB/c mice and grown in 10 ng/ml IL-3 and 10 ng/ml SCF for 4-8 weeks. 1 million BMMCs in triplicates were cultured with 30 µM PACMA-31 (Sigma-Aldrich) for 30 minutes. Some cells were activated by priming cells with DNP-IgE antibodies and challenging with DNP-BSA. Cytokine levels (IL-13, TNF-alpha, and IL-6 in FIGS. 2A-2C) were assessed in the supernatants 6 hrs later by ELISA. FIG. 2A-2C show treatment of mast cells with the specific PDI inhibitor PACMA-31 inhibits the activation of mast cells and the production of mast cell cytokines such as TNF-a, IL-6, and IL-13.

Figure 3A:
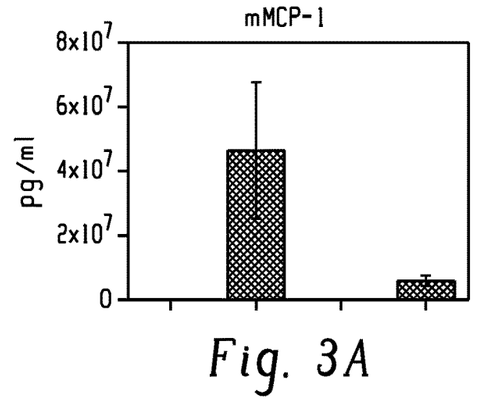
Figure 3B:
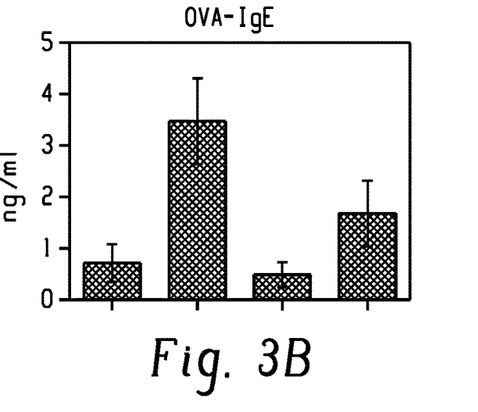
Figure 3C:
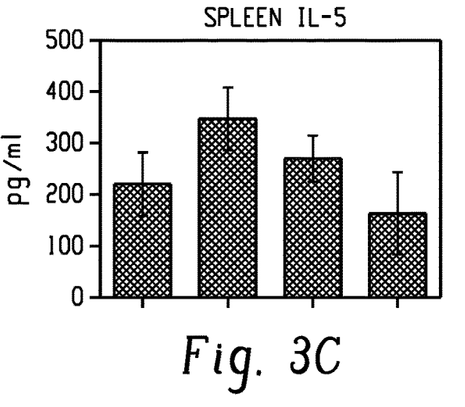
Figure 3D:
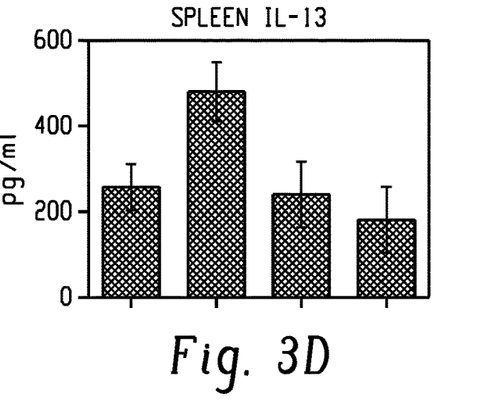
Figure 3E:
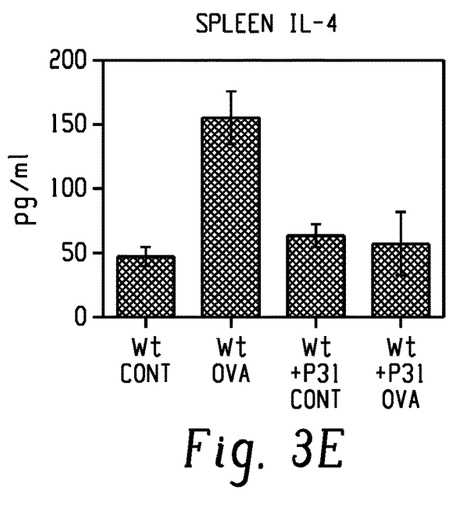
Figure 3F:
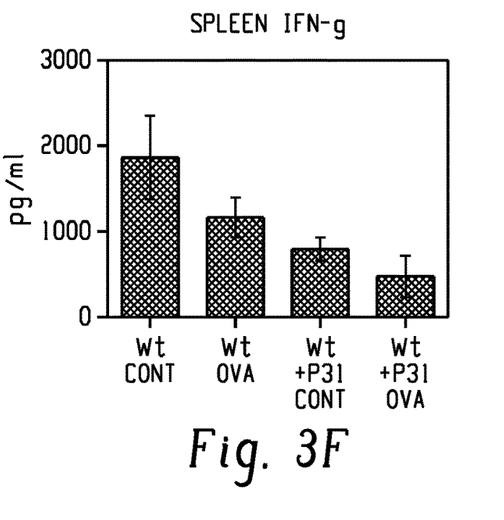

Example 3.: Inhibition of Mast Cell-Mediated Food Allergy in PACMA-31 Treated Mice; Mouse Model of Food Allergy In this study, wild-type (Wt) mice were sensitized and challenged with ovalbumin and treated with PACMA-31 to determine whether PDI inhibition can modulate the development of food allergy. BALB/c mice were sensitized intraperitoneally (i.p.) with 50 µg ovalbumin (OVA) and 1 mg alum on day zero (d0) and d14. On day 28, some groups of mice were challenged intragastrically with 50 mg OVA once a day on 6 alternating days. Some groups of mice were treated with 300 µg PACMA-31 (P-31) intragastrically daily starting d27. One hour after the 6th challenge mice were observed for diarrhea, sacrificed and allergic parameters were evaluated. The development of allergic diarrhea in this model is dependent on mast cell activation. FIG. 3A shows serum mMCP-1 levels; FIG. 3B shows serum OVA-IgE levels; and FIGS. 3C-3F show cytokine levels (IL-5, IL-13, IL-4, and IFN-g) in supernatants of spleen cells restimulated with OVA. In FIGS. 3A-3F, Wt Cont=wild-type, Control; Wt OVA=wild-type, ovalbumin; Wt+P31 Cont=wild-type, PACMA-31, Control; and Wt+P31 OVA=wild-type, PACMA-31, ovalbumin. FIG. 3A-3F show oral treatment of mice undergoing food allergy with PACMA-31 results in attenuation of the allergic response including mast cell protease levels which indicate mast cell activation (mMCP-1), OVA-IgE levels, and Th2 cytokine levels.

The data provided in the Examples demonstrate activation of BMMCS via IgE and antigen resulted in the enhanced expression and secretion of IL-4, IL-6, TNF and IL-13. In contrast, pretreatment with the PDI inhibitors resulted in decreased expression and secretion of these cytokines. Furthermore, treatment of wild-type mice with PACMA-31 in a model of ovalbumin-induced food allergy resulted in a significant attenuation in the development of food allergy symptoms including decreases in allergic diarrhea, mast cell activation and allergen-specific IgE. These data suggest that mast cell activation during allergic responses may be regulated by PDI induction, and that blocking PDI function may prove to be of therapeutic benefit in allergic patients.

The methods disclosed herein include(s) at least the following aspects:

Aspect 1: A method of treating, inhibiting, or preventing the development of, a food allergy in a patient, comprising: administering a therapeutically effective amount of a thiol isomerase inhibitor to a patient in need thereof.

Aspect 2: The method of Aspect 1, wherein the thiol isomerase inhibitor is a PDI inhibitor.

Aspect 3: The method of any one of the preceding Aspects, wherein the thiol isomerase inhibitor is administered to the patient daily for a period of days, weeks, or months.

Aspect 4: The method of any one of the preceding Aspects, wherein the thiol isomerase inhibitor is administered to the patient prior to the patient consuming a food comprising an allergen; or wherein the thiol isomerase inhibitor is administered to the patient with a food comprising an allergen; or wherein the thiol isomerase inhibitor is administered to the patient after the patient has consumed a food comprising an allergen and has experienced a symptom of a food allergy.

Aspect 5: The method of any one of the preceding Aspects, wherein the thiol isomerase inhibitor is administered to the patient at least about 2 hours to about 24 hours before the patient consumes a food.

Aspect 6: The method of any one of the preceding Aspects, wherein the food is cow milk, egg, peanut, a tree nut, corn, soy, wheat, a shell fish, a fish protein, a fruit, rice, or a combination thereof.

Aspect 7: The method of any one of the preceding Aspects, wherein the thiol isomerase inhibitor is a compound in the class of propynoic acid carbamoyl methyl amides (PACMAs), e.g., PACMA 31 (N-(2,4-dimethoxyphenyl)-N-(1-oxo-2-propyn-1-yl)-2-(2-thienyl)glycylglycine ethyl ester); bacitracin; juniferdin; juniferdin epoxide; rutin (rutoside, quercetin-3-O-rutinoside); phenylarsine oxide; LOC14 (2-[[4-(cyclopropylcarbonyl)-1-piperazinyl]methyl]-1,2-benzisothiazol-3(2H)-one); CCF 642 (3-(4-methoxyphenyl)-5-[(5-nitro-2-thienyl)methylene]-2-thioxo-4-thiazolidinone); P1 (N-[(1,1-dimethylethoxy)carbonyl]-L-phenylalanyl-O-(ethenylsulfonyl)-N-4-pentyn-1-yl-L-tyrosinamide); 16F16 (2-(2-chloroacetyl)-2,3,4,9-tetrahydro-1-methyl-1H-pyrido[3,4-b]indole-1-carboxylic acid methyl ester); ML359 (ethyl 1-(3-chloro-4-hydroxybenzyl)-4-(2-phenoxyethyl)piperidine-4-carboxylate); zafirlukast; montelukast; CGP-13501; CGP-7930; alosetron; balsalazide; benserazide; butaclamol; leva-dopa; mesalazine; oxcarbazepine; or combination thereof, optionally in combination with curcumin; or a PDI targeting antibody, such as PDI Antibody (RL90, MA3-019), intravenous immunoglobulin (IVIG), or combinations thereof.

Aspect 8: The method of any one of the preceding Aspects, wherein the thiol isomerase inhibitor is formulated as a pharmaceutical composition in dosage form.

Aspect 9: The method of Aspect 8, wherein the thiol isomerase inhibitor is formulated as a tablet or capsule.

Aspect 10: The method of any one of the preceding Aspects, wherein the thiol isomerase inhibitor is formulated as a pharmaceutical composition suitable for administration orally, topically, parenterally, by inhalation or spray, sublingually, transdermally, via buccal administration, or rectally.

Aspect 11: A method of inhibiting or preventing cytokine production in a patient, the cytokine production caused by a food allergen, the method comprising: administering a therapeutically effective amount of a thiol isomerase inhibitor to a patient in need thereof.

Aspect 12: The method of Aspect 11, wherein the cytokine is tumor necrosis factor, interleukin-4, interleukin-5, interleukin-6, interleukin-13, or a combination thereof.

Aspect 13: The method of Aspect 11 or 12, wherein the thiol isomerase inhibitor is a protein disulfide isomerase (PDI) inhibitor.

Aspect 14: The method of any one of Aspects 11-13, wherein the thiol isomerase inhibitor is a compound in the class of propynoic acid carbamoyl methyl amides (PACMAs), e.g., PACMA 31 (N-(2,4-dimethoxyphenyl)-N-(1-oxo-2-propyn-1-yl)-2-(2-thienyl)glycylglycine ethyl ester); bacitracin; juniferdin; juniferdin epoxide; rutin (rutoside, quercetin-3-O-rutinoside); phenylarsine oxide; LOC14 (2-[[4-(cyclopropylcarbonyl)-1-piperazinyl]methyl]-1,2-benzisothiazol-3(2H)-one); CCF 642 (3-(4-methoxyphenyl)-5-[(5-nitro-2-thienyl)methylene]-2-thioxo-4-thiazolidinone); P1 (N-[(1,1-dimethylethoxy)carbonyl]-L-phenylalanyl-O-(ethenylsulfonyl)-N-4-pentyn-1-yl-L-tyrosinamide); 16F16 (2-(2-chloroacetyl)-2,3,4,9-tetrahydro-1-methyl-1H-pyrido[3,4-b]indole-1-carboxylic acid methyl ester); ML359 (ethyl 1-(3-chloro-4-hydroxybenzyl)-4-(2-phenoxyethyl)piperidine-4-carboxylate); zafirlukast; montelukast; CGP-13501; CGP-7930; alosetron; balsalazide; benserazide; butaclamol; leva-dopa; mesalazine; oxcarbazepine; or combination thereof, optionally in combination with curcumin; or a PDI targeting antibody, such as PDI Antibody (RL90, MA3-019), intravenous immunoglobulin (IVIG), or combinations thereof.

Aspect 15: A method of treating, inhibiting, or preventing the development of, an allergic disease or an inflammatory disease in a patient, comprising: administering a therapeutically effective amount of a thiol isomerase inhibitor to a patient in need thereof.

Aspect 16: The method of Aspect 15, wherein the thiol isomerase inhibitor is a protein disulfide isomerase (PDI) inhibitor.

Aspect 17: The method of Aspect 15, wherein the thiol isomerase inhibitor is a compound in the class of propynoic acid carbamoyl methyl amides (PACMAs), e.g., PACMA 31 (N-(2,4-dimethoxyphenyl)-N-(1-oxo-2-propyn-1-yl)-2-(2-thienyl)glycylglycine ethyl ester); bacitracin; juniferdin; juniferdin epoxide; rutin (rutoside, quercetin-3-O-rutinoside); phenylarsine oxide; LOC14 (2-[[4-(cyclopropylcarbonyl)-1-piperazinyl]methyl]-1,2-benzisothiazol-3(2H)-one); CCF 642 (3-(4-methoxyphenyl)-5-[(5-nitro-2-thienyl)methylene]-2-thioxo-4-thiazolidinone); P1 (N-[(1,1-dimethylethoxy)carbonyl]-L-phenylalanyl-O-(ethenylsulfonyl)-N-4-pentyn-1-yl-L-tyrosinamide); 16F16 (2-(2-chloroacetyl)-2,3,4,9-tetrahydro-1-methyl-1H-pyrido[3,4-b]indole-1-carboxylic acid methyl ester); ML359 (ethyl 1-(3-chloro-4-hydroxybenzyl)-4-(2-phenoxyethyl)piperidine-4-carboxylate); zafirlukast; montelukast; CGP-13501; CGP-7930; alosetron; balsalazide; benserazide; butaclamol; levadopa; mesalazine; oxcarbazepine; or combination thereof, optionally in combination with curcumin; or a PDI targeting antibody, such as PDI Antibody (RL90, MA3-019), intravenous immunoglobulin (IVIG), or combinations thereof.

Aspect 18: The method of any one of Aspects 15-17, wherein the thiol isomerase inhibitor is formulated as a pharmaceutical composition in dosage form.

Aspect 19: The method of any one of Aspects 15-17, wherein the thiol isomerase inhibitor is formulated as a pharmaceutical composition suitable for administration orally, topically, parenterally, by inhalation or spray, sublingually, transdermally, via buccal administration, or rectally.

Unless defined otherwise, technical and scientific terms used herein have the same meaning as is commonly understood by one of skill in the art to which this disclosure belongs.

The singular forms "a," "an," and "the" include plural referents unless the context clearly dictates otherwise. The endpoints of all ranges directed to the same characteristic or component are independently combinable and inclusive of the recited endpoint. The suffix "(s)" as used herein is intended to include both the singular and the plural of the term that it modifies, thereby including one or more of that term (e.g., the carrier(s) includes one or more carriers). The term "or" means "and/or" unless clearly indicated otherwise by context. The term "combination" is inclusive of blends, mixtures, and the like.

Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments.

In general, the compositions, methods, and articles can alternatively comprise, consist of, or consist essentially of, any ingredients, steps, or components herein disclosed. The compositions, methods, and articles can additionally, or alternatively, be formulated, conducted, or manufactured so as to be devoid, or substantially free, of any ingredients, steps, or components not necessary to the achievement of the function or objectives of the present claims.

"Optional" or "optionally" means that the subsequently described event or circumstance may or may not occur, and that the description includes instances where the event occurs and instances where it does not.

"About" or "approximately" as used herein is inclusive of the stated value and means within an acceptable range of deviation for the particular value as determined by one of ordinary skill in the art, considering the measurement in question and the error associated with measurement of the particular quantity (e.g., the limitations of the measurement system). For example, "about" can mean within one or more standard deviations.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention can include only some of the described embodiments. Accordingly, the invention is not to be seen as limited by the foregoing description, but is only limited by the scope of the appended claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

The invention claimed is:

1. A method of treating, inhibiting, or preventing the development of a food allergy in a patient, comprising: administering a therapeutically effective amount of two thiol isomerase inhibitors to a patient in need thereof;
    wherein the thiol isomerase inhibitor is a protein disulfide isomerase inhibitor; and wherein the thiol isomerase inhibitor is a compound in the class of propynoic acid carbamoyl methyl amides (PACMAs) selected from the group consisting of PACMA 31 (N-(2,4-dimethoxypheny 1)-N-(1-oxo-2- propyn-1-yl)-2-(2-thienyl) glycylglycine ethyl ester); juniferdin; juniferdin epoxide; phenylarsine oxide; LOC 14 (2-1 14-(cyclopropylcarbonyl)-1-piperazinyllmethy 11-1,2-benzisothiazol-3(2H)-one); CCF 642 (3-(4-methoxypheny 1)-5- 1(5-nitro-2- thienyl)methylene 1-2-thioxo-4-thiazolidinone); P1 (N- 1(1,1-dimethylethoxy)carbonyll-L - phenylalanyl1-O -(ethenylsulfonyl1)-N-4-pentyn-1-yl-L-tyrosinamide); 1 6F1 6 (2-(2-chloroacety 1)-2,3 ,4,9-tetrahydro-1-methyl-1H-pyrido13,4-blindole-1-carboxylic acid methyl ester); ML359 (ethyl 1- (3-chloro-4-hydroxybenzy 1)-4-(2-phenoxyethyl)piperidine-4- carboxylate); zafirlukast; CGP -13501; CGP-7930; alosetron; balsalazide; benserazide; butaclamol; oxcarbazepine; or combination thereof, or a protein disulfide isomerase inhibitor targeting antibody, selected from the group consisting of protein disulfide isomerase inhibitor antibody RL90, or MA3-0 19 and wherein the therapeutically effective amount of the two thiol isomerase inhibitors are formulated as a pharmaceutical composition suitable for administration orally, parenterally, or transdermally.

2. The method of claim 1, wherein the pharmaceutical composition comprising the two thiol isomerase inhibitors is administered to the patient daily for a period of days, weeks, or months.

3. The method of claim 1, wherein the pharmaceutical composition comprising the two thiol isomerase inhibitors is administered to the patient prior to the patient consuming a food comprising an allergen; or wherein the pharmaceutical composition comprising the two thiol isomerase inhibitors is administered to the patient with a food comprising an allergen; or wherein the pharmaceutical composition comprising the two thiol isomerase inhibitors is administered to the patient after the patient has consumed a food comprising an allergen and has experienced a symptom of a food allergy.

4. The method of claim 1, wherein the pharmaceutical composition comprising the two thiol isomerase inhibitors is administered to the patient at least about 2 hours to about 24 hours before the patient consumes a food.

5. The method of claim 4, wherein the food is cow milk, egg, peanut, a tree nut, corn, soy, wheat, a shell fish, a fish protein, a fruit, rice, or a combination thereof.

6. The method of claim 1, wherein the pharmaceutical composition comprising the two thiol isomerase inhibitors is formulated as a pharmaceutical composition in dosage form.

7. The method of claim 6, wherein the pharmaceutical composition comprising the two thiol isomerase inhibitors is formulated as a tablet or capsule.

8. A method of inhibiting or preventing cytokine production in a patient, the cytokine production caused by a food allergen, the method comprising: administering a therapeutically effective amount of two thiol isomerase inhibitors to a patient in need thereof; wherein the thiol isomerase inhibitor is a protein disulfide isomerase (PDI) inhibitor; and wherein the thiol isomerase inhibitor is a compound in the class of propynoic acid carbamoyl methyl amides (PACMAs) selected from the group consisting of PACMA 31 (N-(2,4-dimethoxypheny 1)-N-(1-oxo-2- propyn-1-yl)-2-(2-thienyl)glycylglycine ethyl ester); juniferdin; juniferdin epoxide; phenylarsine oxide; LOC 14 (2-[[4-(cyclopropyl-carbonyl)-1-piperazinyl]methy 1]-1,2-benzisothiazol-3(2H)-one); CCF 642 (3-(4-methoxypheny 1)-5-[(5-nitro-2-thienyl)methylene 1-2-thioxo-4-thiazolidinone); P1 (N-[(1,1-dimethylethoxy)carbonyl]-L- phenylalanyl1-O-(ethe-nylsulfonyl1)-N-4-pentyn-1-yl-L -tyrosinamide); 1 6F1 6 (2-(2- chloroacety 1)-2,3 ,4,9-tetrahydro-1-methyl-1H-pyrido[3,4-b]indole-1-carboxylic acid methyl ester); ML359 (ethyl 1 -(3-chloro-4-hydroxybenzy 1)-4-(2-phe-noxyethyl)piperidine-4- carboxylate); zafirlukast; CGP-13501; CGP-7930; alosetron; balsalazide; benserazide; butaclamol; oxcarbazepine; or combination thereof, or a protein disulfide isomerase inhibitor targeting antibody, selected from the group consisting of protein disulfide isomerase inhibitor antibody RL90, or MA3-0 19, and wherein the therapeutically effective amount of the two thiol isomerase inhibitors is formulated as a pharmaceutical composition suitable for administration orally, parenterally, by inhalation or spray, transdermally, or rectally.

9. The method of claim 8, wherein the cytokine is tumor necrosis factor, interleukin-4, interleukin-5, interleukin-6, interleukin-13, or a combination thereof.

* * * * *